United States Patent [19]

Elabbady et al.

[11] Patent Number: 5,999,852
[45] Date of Patent: Dec. 7, 1999

[54] DEFIBRILLATOR METHOD AND APPARATUS

[75] Inventors: Tarek Z. Elabbady, Redmond; Fred W. Chapman, Renton; Joseph L. Sullivan, Kirkland; Richard C. Nova, Kirkland; Lawrence A. Borschowa, Kirkland, all of Wash.

[73] Assignee: Physio-Control Manufacturing Corporation, Redmond, Wash.

[21] Appl. No.: 09/062,192

[22] Filed: Apr. 17, 1998

Related U.S. Application Data

[63] Continuation-in-part of application No. 08/844,572, Apr. 18, 1997, abandoned.

[51] Int. Cl.$^6$ .................................................. A61N 1/39
[52] U.S. Cl. ................................................................ 607/8
[58] Field of Search .................................. 607/5, 7, 8, 28

[56] References Cited

U.S. PATENT DOCUMENTS

| | | |
|---|---|---|
| 3,860,009 | 1/1975 | Bell et al. . |
| 3,886,950 | 6/1975 | Ukkestad et al. . |
| 4,328,808 | 5/1982 | Charbonnier et al. . |
| 4,574,810 | 3/1986 | Lerman . |
| 4,771,781 | 9/1988 | Lerman . |
| 4,840,177 | 6/1989 | Charbonnier et al. . |
| 5,088,489 | 2/1992 | Lerman . |
| 5,111,813 | 5/1992 | Charbonnier et al. . |
| 5,215,081 | 6/1993 | Ostroff ........................................ 607/8 |
| 5,230,336 | 7/1993 | Fain et al. . |
| 5,243,975 | 9/1993 | Alferness et al. ........................... 607/7 |

(List continued on next page.)

FOREIGN PATENT DOCUMENTS

WO 95/05215  2/1995  WIPO .

OTHER PUBLICATIONS

Laboratory Investigation—Defibrillation, Automated impedance–based energy adjustment for defibrillation: experimental studies, Richard E. Kerber, M.D., David McPherson, M.D., Francis Charbonnier, Ph.D., Robert Kieso, M.S., and Pamela Hite, B.S., *Circulation*, vol. 71, No. 1, Jan. 1985.

Therapy and Prevention—Arrhythmia, Energy, current, and success in defibrillation and cardioversion: clinical studies using an automated impedance–based method of energy adjustment, Richard E. Kerber, M.D., James B. Martins, M.D., Michael G. Kienzle, M.D., Luis Constantin, M.D., Brian Olshansky, M.D., Roseanne Hopson, R.N., and Francis Charbonnier, Ph.D., *Circulation*, vol. 77, No. 5, May 1988.

Current–Based Versus Energy–Based Ventricular Defibrillation: A Prospective Study, Bruce B. Lerman, MD, FACC, John P. DiMarco, MD, PhD, FACC, and David E. Haines, MD, *JACC*, vol. 12, No. 5, Nov. 1988; 12:1259–64.

(List continued on next page.)

*Primary Examiner*—William E. Kamm
*Assistant Examiner*—George R. Evanisko
*Attorney, Agent, or Firm*—Christensen O'Connor Johnson & Kindness PLLC

[57] ABSTRACT

A defibrillator method and apparatus wherein a patient's measured transthoracic impedance (TTI) is used to control the amount of energy contained in a defibrillation pulse applied to the patient. Prior to delivering a defibrillation pulse, the patient's TTI is measured by an impedance measuring circuit (11). The patient's TTI may also be measured during delivery of a prior defibrillation pulse. A microprocessor (23) uses the measured patient TTI to control the shape of the defibrillation pulse by controlling: (i) the phase duration of the defibrillation pulse; and (ii) the voltage level to which the defibrillator's capacitor bank (15) is charged. The defibrillation pulse shape is controlled so that the energy conveyed by the defibrillation pulse to the patient is near or exceeds a desired value. The desired value may be set by an operator via an energy selector (25). A switch (13) controls the connection of defibrillator electrodes (27a, 27b) to the impedance measuring circuit (11) and the capacitor bank (15).

20 Claims, 7 Drawing Sheets

U.S. PATENT DOCUMENTS

| | | |
|---|---|---|
| 5,344,430 | 9/1994 | Berg et al. . |
| 5,431,687 | 7/1995 | Kroll . |
| 5,474,574 | 12/1995 | Payne et al. . |
| 5,540,723 | 7/1996 | Ideker et al. . |
| 5,540,724 | 7/1996 | Cox . |
| 5,593,427 | 1/1997 | Gliner et al. . |
| 5,601,612 | 2/1997 | Gliner et al. . |
| 5,607,454 | 3/1997 | Cameron et al. . |
| 5,891,173 | 4/1999 | Brewer . |

OTHER PUBLICATIONS

Choosing the Optimal Monophasic and Biphasic Waveforms for Ventricular Defibrillation, Gregory P. Walcott, M.D., Robert G. Walker, B.A., Adam W. Cates, B.S.B.M.E., Wanda Krassowska, Ph.D., William M. Smith, Ph.D. and Raymond E. Ideker, M.D., Ph.D., *Journal of Cardiovascular Electrophysiology*, vol. 6, No. 9, Sep. 1995.

DEFIBRILLATOR METHOD AND APPARATUS

CROSS-REFERENCE TO RELATED APPLICATION

This application is a continuation-in-part of prior U.S. application Ser. No. 08/844,572, filed Apr. 18, 1997, now abandoned, priority from the filing date of which is hereby claimed under 35 U.S.C. § 120.

FIELD OF THE INVENTION

The invention relates generally to methods and apparatus for delivering defibrillating energy to a patient and, more particularly, to methods and apparatus for delivering defibrillating energy to patients with different transthoracic impedance.

BACKGROUND OF THE INVENTION

Ventricular fibrillation is one of the most common life-threatening medical conditions that occurs with respect to the human heart. In ventricular fibrillation, the human heart's electrical activity becomes unsynchronized, which results in a loss of its ability to contract. As a result, a fibrillating heart immediately loses its ability to pump blood into the circulation system. A common treatment for ventricular fibrillation is to apply an electric pulse to the heart that is strong enough to stop the unsynchronized electrical activity and give the heart's natural pacemaker a chance to reinitiate a synchronized rhythm. External defibrillation is the method of applying the electric pulse to the fibrillating heart through a patient's thorax.

Existing external cardiac defibrillators first accumulate a high-energy electric charge in an energy store, typically a capacitor. When a switching mechanism is activated, the stored energy is applied to the patient via electrodes positioned on the patient's thorax. The resultant discharge of the capacitor causes a large current pulse to be transferred through the patient.

Circuitry in a defibrillator may be used to alter a pulse's duration and direction of flow, thereby affecting the shape of the pulse. Common defibrillating pulse shapes include damped sine and truncated exponential waveforms. Both types of waveforms can have single or multiple phases. A biphasic truncated exponential waveform has two phases. In the first phase of the pulse, current flows in one direction. In the second phase, current flows in the opposite direction.

Regardless of the waveform used by a defibrillator, the defibrillation pulse applied to a patient contains a certain amount of energy. The defibrillator industry uses energy settings on a defibrillator's control panel to indicate the selected amount of energy that the defibrillation pulse should deliver to the patient.

In existing defibrillation practice, when it is necessary to apply a succession of defibrillation pulses to a patient, the operator generally increases the selected amount of energy to be delivered by each successive pulse. Higher energy defibrillation pulses are used until defibrillation occurs, or the highest available energy is used. The American Heart Association recommends that an energy level of 200 joules be set for a first defibrillation pulse, 200 or 300 joules for a second defibrillation pulse, and 360 joules for a third defibrillation pulse.

When a defibrillating pulse is applied to a patient, the pulse encounters a resistance to the flow of electrical current through the patient. The resistance of a patient's thorax to the flow of electrical current is called transthoracic impedance (TTI). The magnitude of current flowing through a patient is directly proportional to the magnitude of the voltage difference across the electrodes used to deliver the defibrillation pulse to the patient and inversely proportional to the patient's TTI.

External defibrillators are likely to encounter patients with a wide range of TTI values. Thus, one challenge that faces external defibrillator manufacturers is to design defibrillators that work well over a wide range of patient TTI values. While conventional defibrillators are often specified for and tested with 50 ohm loads, patient TTI can vary greatly in a range from 25 to 180 ohms. Average patient TTI in a hospital setting is about 80 ohms.

Defibrillator circuits which generate damped sine and truncated exponential pulses respond differently to variations in transthoracic impedance. Damped sine defibrillator impedance response is passive; that is, the response is determined entirely by the amount of capacitance, inductance, and resistance in the circuit. As impedance increases, defibrillating pulse duration increases and peak current decreases.

Several factors affect the shape of waveforms produced by truncated exponential defibrillators in response to different TTI values. Both the capacitance and resistance of the circuit determine passively how quickly the current drops after its initial peak. The active control of a switch that truncates the discharge determines the duration of each phase of the pulse. By design, pulse duration typically increases with increasing TTI values. This is done to allow additional time for energy delivery before the pulse is truncated.

Prior art defibrillators are calibrated for energy delivery at a single, specified load impedance, typically 50 ohms. However, as noted earlier, the TTI of many patients exceeds 50 ohms. As a result, the amount of energy actually delivered to a patient is different than the energy level selected by the operator. With damped sine waveforms, patients with TTI greater than 50 ohms receive higher energy than the energy level selected by the operator. With truncated exponential waveforms having fixed durations, patients with TTI greater than 50 ohms receive less energy than the selected energy level. The peak current delivered to patients also drops as patient TTI increases. Prior art defibrillators using truncated exponential waveforms typically adjust the duration of the waveforms (i.e., increased duration with increased impedance) to compensate for a decrease in energy delivered. However, partly because of a reduction in peak current produced in higher impedance patients, long duration truncated exponential waveforms may be less effective among high impedance patients. See, for example, the article "Transthoracic Defibrillation of Swine with Monophasic and Biphasic Waveforms," *Circulation* 1995, Vol. 92, p. 1634, in which the authors Gliner et al. acknowledge that, for a biphasic truncated exponential waveform, pulse durations exceeding 20 milliseconds are less effective.

Recognizing that patient TTI values affect the amount of current actually delivered to a patient, the prior art has proposed various techniques designed to compensate for varying patient impedance values. For example, U.S. Pat. No. 4,574,810 to Lerman discloses a defibrillator designed to provide a peak current using an amperes per ohm factor based on a measured patient transthoracic resistance. U.S. Pat. Nos. 4,771,781 and 5,088,489, also to Lerman, disclose current-based defibrillation methods. These prior art defibrillation methods include first determining the patient's transthoracic resistance and then discharging a capacitor with the intent that the peak current preselected by the operator as appropriate for attaining defibrillation is delivered. An article related to this prior art technique is found at Lerman et al., "Current-Based Versus Energy-Based Ventricular Defibrillation: A Prospective Study," *Journal of the American College of Cardiology*, November 1988, Vol. 12, No. 5, page 1259. U.S. Pat. No. 4,840,177 to Charbonnier et al. discloses a method and apparatus wherein a patient's measured impedance is normalized and multiplied by a desired current to yield a target charge level for an energy storage device to induce the desired current in the patient on discharge. These prior art techniques focus on delivering a desired current rather than tailoring a defibrillation pulse shape to optimally deliver a desired amount of energy.

Another prior art technique in which adjustments are made in response to measured patient TTI is disclosed by Kerber et al. in "Automated impedance-based energy adjustment for defibrillation: experimental studies," *Circulation*, January 1985, Vol. 71, No. 1, page 136; and "Energy, current, and success in defibrillation and cardioversion: clinical studies using an automated impedance-based method of energy adjustment," *Circulation*, May 1988, Vol. 77, No. 5, page 1038. In these articles, the authors address the problem of providing an adequate amount of energy for defibrillation to different patients having high and low transthoracic impedance. The authors suggest basing a first defibrillation pulse on a low energy value, such as 100 joules. The authors believe that delivery of such a pulse to a low impedance patient may be sufficient for defibrillation. To address higher impedance patients, the authors suggest measuring patient impedance momentarily before defibrillation to determine if the patient impedance exceeds an arbitrary value such as 70 ohms. If a patient impedance in excess of 70 ohms is detected, the authors suggest automatically increasing the selected amount of energy.

For example, if a 100-joule pulse is selected by an operator, a defibrillation pulse of 200 joules would be delivered if the patient's TTI exceeded 70 ohms. Likewise, if 150 joules or 200 joules is selected, the defibrillator would deliver 300 joules or 400 joules, respectively. The authors' proposal is based on a belief that low energy defibrillation pulses are insufficient to defibrillate high impedance patients and that applying a higher energy first pulse to such patients will avoid the need to apply multiple defibrillation pulses.

Delivering different levels of energy to patients having different TTI levels is also disclosed in U.S. Pat. No. 5,111,813 to Charbonnier et al. An impedance-dependent delivered energy is derived by multiplying a patient's TTI by a parameter $E_d/Z_p$ measured in joules per ohm. Accordingly, patients having lower TTI will receive a lower amount of energy while higher TTI patients receiver higher energy. This technique is not concerned with delivering a selected amount of energy to patients across the range of potential patient impedance.

Another prior art technique for dealing with differing patient TTI involves detecting the patient's actual transthoracic impedance during delivery of the first defibrillation shock. In U.S. Pat. No. 4,328,808 to Charbonnier et al. an alarm is activated if the detected TTI exceeds a predetermined value. The alarm notifies the operator of the need to increase the selected amount of energy before applying another defibrillation pulse.

Other prior art techniques to compensate for different patient TTI have involved altering the duration of the defibrillation pulse. For example, U.S. Pat. No. 5,230,336 to Fain et al. discloses a method of selecting a suggested pulse width for a second defibrillation pulse based on system impedance measured during delivery of a first defibrillation pulse. U.S. Pat. Nos. 5,601,612 and 5,593,427, both to Gliner et al., describe on-the-fly adjustment to the duration of a defibrillation pulse to compensate for patient-to-patient impedance differences. U.S. Pat. No. 5,540,723 to Ideker et al. discloses methods and apparatus for treating cardiac arrhythmias wherein the duration of a defibrillation pulse is adjusted in accordance with a detected pulse signal time constant, of which patient impedance is one factor. U.S. Pat. No. 5,607,454 to Cameron et al. teaches on-the-fly adjustment to the relative duration of phases of a multiphasic waveform depending on a monitored parameter detected during delivery of the waveform to a patient. U.S. Pat. No. 5,534,015 to Kroll et al. discloses an implantable defibrillator that uses a resistance value measured across electrodes to dynamically control the duration of a first portion of a multiphasic waveform's first phase. Nevertheless, compensating for increased patient TTI by increasing the duration of the defibrillation pulse after delivery of the pulse has begun is not satisfactory because in cases where there is insufficient charge on the capacitor, the current delivered by such a defibrillation pulse is not sufficient to defibrillate the heart, especially when a monophasic or biphasic truncated exponential waveform is employed.

While the prior art has recognized that defibrillator pulse current, energy, and shape are related to patient TTI, the prior art has not suggested that, particularly for truncated exponential defibrillation pulses, the shape of the pulse, including peak amplitude and phase duration should be adjusted according to patient TTI measured prior to delivery to assure delivery of a chosen amount of energy. The present invention is directed to providing a defibrillation method and apparatus wherein the amplitude and duration of a defibrillation pulse are determined prior to delivery based on a measured patient TTI so that the energy conveyed by a defibrillation pulse to the patient is near or exceeds the selected level regardless of the patient's TTI.

SUMMARY OF THE INVENTION

In accordance with the present invention, a defibrillator method and apparatus are provided wherein a patient's transthoracic impedance (TTI) is measured prior to delivery of a defibrillation pulse. The patient's TTI is used to control the shape (amplitude and duration) of a defibrillation pulse, and hence control the amount of energy conveyed by the defibrillation pulse to the patient. More specifically, a patient's TTI is measured prior to charging a defibrillator's energy store for delivery of a defibrillation pulse. The patient's TTI is also measured during delivery of a defibrillation pulse. The defibrillator method and apparatus of the present invention use the patient's TTI to control the amplitude and duration of the defibrillation pulse, so that the amount of energy conveyed by the defibrillation pulse to the patient is near or exceeds a desired value. Specifically, an optimal pulse duration is determined and a target charge level is set for charging the defibrillator's energy store so that the defibrillation pulse having the determined duration conveys the amount of energy desired. The desired energy value can be chosen by an operator, or can be automatically determined by the defibrillator based on the patient's TTI value.

Because the amplitude of a defibrillation pulse is directly related to the level to which a defibrillator's energy store is charged, in accordance with further aspects of this invention, the defibrillator controls the shape of a defibrillation pulse by adjusting the charge stored in the energy store. Preferably, the energy store is a capacitor bank and the defibrillator charges the capacitor bank to a voltage level determined by using the patient's measured TTI value as an index to a look-up table containing voltage level information. The look-up table is stored in a memory and associates patient TTI values with voltage levels. The looked-up value is used to control the charging of the defibrillator's energy store so that a defibrillation pulse produced by discharging the energy store conveys an amount of energy to a patient that is near or exceeds a chosen amount of energy.

In accordance with other aspects of this invention, the defibrillator also shapes the defibrillation pulse by controlling the duration of one or more phases of the pulse prior to delivering the pulse to a patient. Preferably, the defibrillation pulse has a biphasic truncated exponential (BTE) shape. The duration of the first phase of the BTE pulse is determined by using the patient's measured TTI as an index to a look-up table of phase durations stored in a memory. While the duration of the second phase of the BTE pulse may be similarly determined from a look-up table, preferably the duration of the second phase is set to be two-thirds of the duration of the first phase.

In accordance with yet other aspects of this invention, the defibrillator uses different measurements of a patient's TTI to detect whether the defibrillator-patient connection is in an open or shorted state that could prevent delivery of the desired energy to the patient. An open or shorted state exists whenever the measured impedance falls outside a range of normal patient TTI values (e.g., 25–300 ohms). When an open or shorted connection is detected, the defibrillator either discharges the stored energy into an internal energy dump or prevents the energy store from producing a defibrillation pulse.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
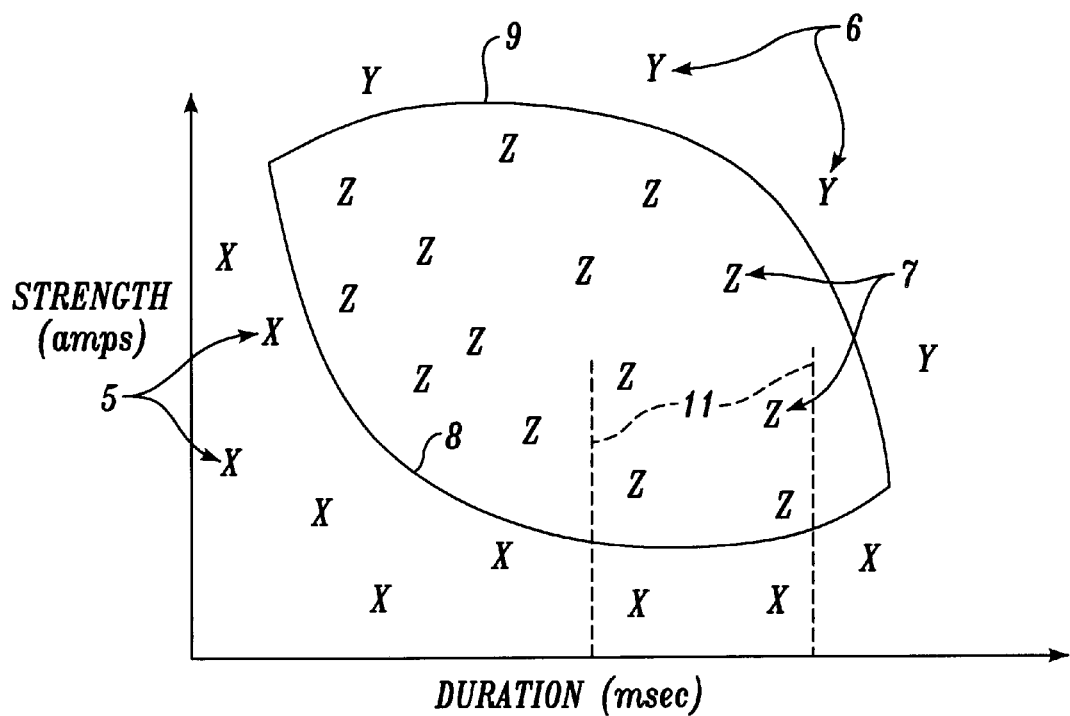
FIG. 1 is a strength-duration graph depicting defibrillation pulse efficacy for delivery of a defibrillation pulse to a patient.

The ability of a defibrillation pulse to defibrillate a patient's heart is typically defined in terms of probabilities. A defibrillation pulse having a particular amplitude and duration may be more or less likely to successfully defibrillate a fibrillating heart. The efficacy of a defibrillation pulse delivered to a patient may be expressed in a strength-duration graph as shown in FIG. 1. The strength (amplitude) of a defibrillation pulse, shown in FIG. 1 as amperes of current, is plotted on the y-axis while the duration of the pulse, shown in milliseconds, is plotted on the x-axis. For a given pulse strength and duration, there is a probability that the pulse will succeed in terminating fibrillation of the patient's heart. Defibrillation pulses having too little strength or too little duration, as noted by the X's 5, will likely fail in terminating fibrillation. Defibrillation pulses having too great strength and/or too long duration, as noted by the Y's 6, will likely damage a patient physiologically and/or cause the patient's heart to refibrillate. Accordingly, there is a range of pulse strength and duration, as shown by the Z's 7, in which a defibrillation pulse is more likely to succeed in defibrillating a heart while avoiding long-term damage or refibrillation. Moreover, according to the present invention, an optimal pulse duration is selected to minimize the pulse strength needed for successful defibrillation. In terms of the strength-duration graph of FIG. 1, the optimal duration lies in the range between the dashed lines 11.

A minimum strength-duration threshold, shown by curve 8, identifies the point of crossover from defibrillation pulses that are less likely to more likely result in successful defibrillation. A maximum strength-duration threshold, shown by curve 9, identifies the crossover from successful defibrillation pulses to pulses that are more likely to cause damage or refibrillate the heart. The present invention is directed to optimally shaping one or more defibrillation pulses so that the strength and the duration of a pulse, as delivered to a patient, lies within a range that falls between the threshold curves 8 and 9 for the patient. The present invention uses a measure of the patient's transthoracic impedance (TTI) determined prior to delivery of a defibrillation pulse to tailor the amplitude and duration to the particular patient's TTI.

Before discussing a preferred embodiment of the invention in detail, a brief overview of the invention is provided. When a user attaches a defibrillator constructed according to the invention to a patient and instructs the defibrillator to provide a defibrillation pulse, the defibrillator measures the TTI of the patient prior to delivering the defibrillation pulse. The patient's TTI may be measured outside of defibrillation by a specialized impedance measuring circuit, during delivery of a prior defibrillation pulse from an electrical parameter sensed during the delivery, or a combination of the two. The patient's TTI is used to shape the defibrillation pulse by determining the level to which the energy store included in the defibrillator is charged (thereby determining the strength or amplitude of the pulse) and the period of time the stored energy will be discharged to the patient (thereby determining the duration of the pulse). In a preferred embodiment of the invention, the charge level and phase durations are determined from one or more look-up tables stored in a memory that use patient TTI as an index. The charge level and phase duration values stored in the tables are predetermined such that for each level of patient TTI, the defibrillator produces a defibrillation pulse whose amplitude and duration are such that the defibrillation pulse contains an amount of energy equal to the chosen amount of energy.

Figure 2:
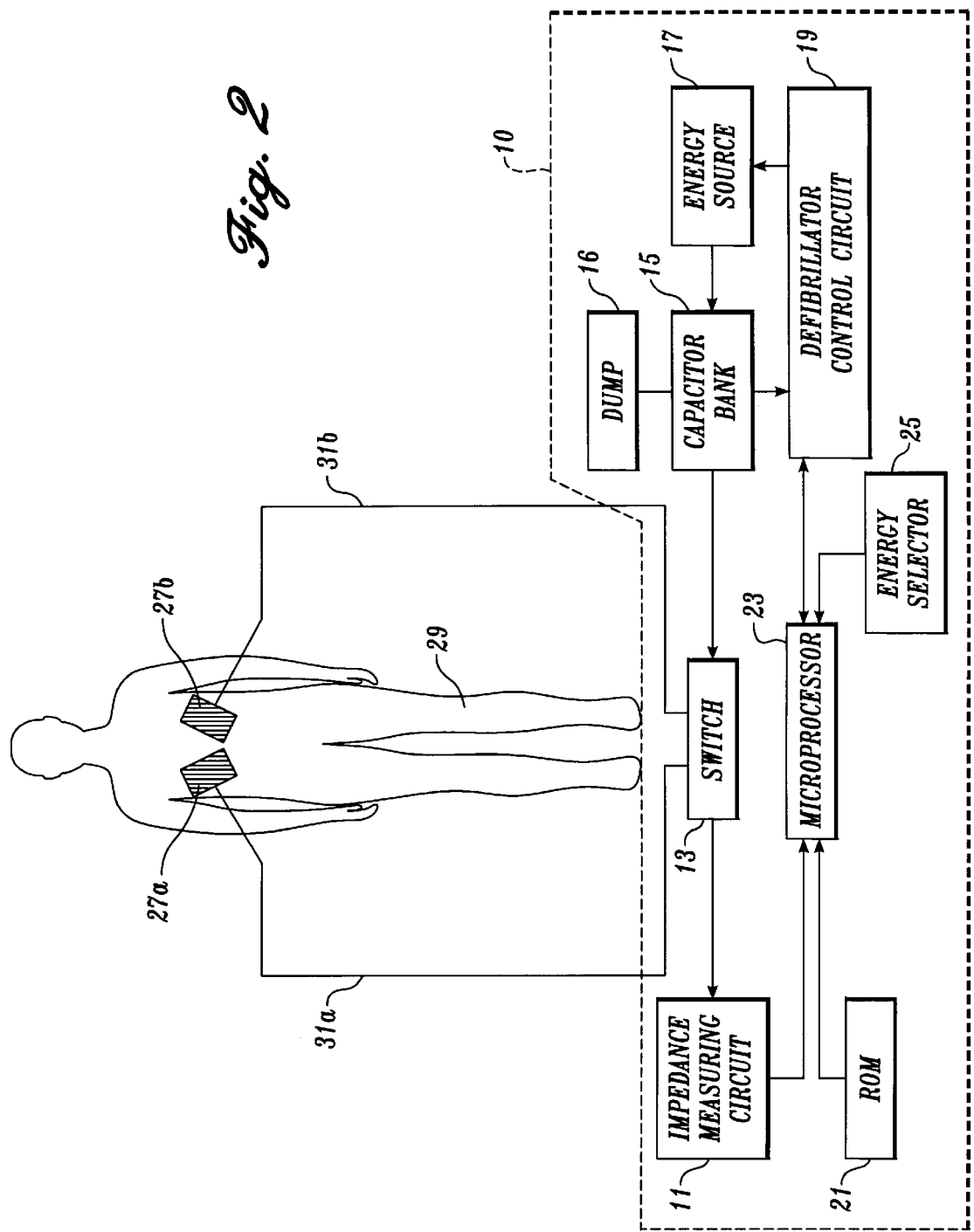
FIG. 2 is a block diagram of a defibrillator formed in accordance with the present invention and connected to a patient for defibrillation.

FIG. 2 is a block diagram illustrating components of a defibrillator 10 formed in accordance with the present invention. The defibrillator 10 includes an impedance measuring circuit 11, a switch 13, a capacitor bank 15, an energy dump 16, an energy source 17, a defibrillator control circuit 19, a memory 21, a microprocessor 23, an energy selector 25, and patient electrodes 27a and 27b.

The patient electrodes 27a and 27b may be hand-held electrode paddles or adhesive electrode pads placed on the skin of a patient. The patient's body provides an electrical path between the electrodes. When using hand-held electrode paddles, the defibrillator preferably prompts the operator to hold and retain the paddles firmly on the patient's thorax throughout the impedance measurement and defibrillation procedure of the present invention.

The energy selector 25 supplies energy setting information to the microprocessor 23 and instructs the defibrillator regarding the defibrillation pulse energy to be delivered to a patient. While the energy selector 25 can be in the form of a continuous dial, in a preferred embodiment the energy selector 25 permits selection of an energy level from a set number of discrete energy levels, such as 100 joules, 200 joules, 300 joules, and 360 joules, for example. If desired, such as in the case of an automated external defibrillator with preprogrammed energy levels, the energy selector 25 could be eliminated.

The patient electrodes 27a and 27b are connected to the switch 13 via conductors 31a and 31b. The switch 13 couples the electrodes 27a and 27b to either the input of the impedance measuring circuit 11 or to the output of the capacitor bank 15, based on the state of a control signal received from the microprocessor 23. The switch is of conventional design and may be formed of electrically-operated relays. Alternatively, an arrangement of solid state devices such as silicon controlled rectifiers or insulated gate bipolar transistors may be used.

According to one aspect of the invention, the defibrillator 10 measures the TTI of a patient (i.e., the impedance between the electrodes 27a and 27b when placed on a patient 29) before delivering a defibrillation pulse. The defibrillator 10 uses the impedance measuring circuit 11 to measure the patient's TTI. The impedance measuring circuit 11 may use any of the known transthoracic impedance measuring techniques, including a high frequency, low level current pulse technique, a sensing resistance technique, or a low intensity sensing shock technique.

Preferably, a high frequency, low level current technique is used for TTI measurement outside of delivering a defibrillation pulse. A pulse generator (not shown) included in the impedance measuring circuit 11 produces low amplitude, constant current high frequency pulses. The pulses are generated at a frequency of up to 50 kHz, preferably around 25 kHz. The pulses flow from one patient electrode 27a through the patient's body to the other patient electrode 27b. This current flow causes a voltage to develop across the patient's body that is proportional to the product of the patient's TTI and the applied current. The impedance measuring circuit 11 measures the voltage, and either the microprocessor 23 or the impedance measuring circuit 11 divides the measurement by the applied current to calculate of the patient's TTI. If the microprocessor 23 performs the calculations, the sensed current and response voltage are provided to the microprocessor in digital form through appropriate A/D converters (not shown).

Measurement of patient TTI may also be accomplished using an electrical parameter sensed by the defibrillator 10 during prior defibrillation pulses, if any, delivered to the patient. Such impedance measurement may include an analysis of the voltage and current that develops in the patient during delivery of the prior defibrillator pulse. Alternatively, it may include an analysis of the drop in capacitor voltage over a period of time during the discharge. Given a known capacitance and resistance internal to the defibrillator 10, one skilled in the art can determine the patient's impedance that contributes to the capacitor voltage rate of decay. The microprocessor 23 may monitor the capacitor bank 15 via the defibrillator control circuit 19.

In some circumstances, it may be advantageous to combine TTI measurements made during prior defibrillation pulses with predefibrillation TTI measurements made by the impedance measuring circuit 11. The combination TTI measurement is used to determine the amplitude and duration of the defibrillation pulse to be delivered (though this is not possible for a first defibrillation pulse because there are no prior defibrillation pulses). In circumstances where a patient TTI measurement made by the impedance measuring circuit 11 before delivery of a defibrillation pulse is believed to be more accurate than a measurement made during delivery of a prior defibrillation pulse, the defibrillator 10 preferably uses the more recent patient TTI value measured by the impedance measuring circuit 11 to control the shape of the pulse.

The defibrillator 10 delivers defibrillating energy to a patient in a defibrillation pulse having a shape that is determined by the defibrillator prior to delivery of the pulse. The amount of energy that a defibrillation pulse delivers to a patient having a particular TTI is controlled by controlling the shape of the defibrillation pulse. Defibrillation pulse shape is determined, in part, by the amplitude and duration of the pulse. Because the amount of energy in a defibrillation pulse is dependent on the shape of the pulse, modification of the shape of a defibrillation pulse can change the amount of energy delivered to a patient. The amplitude of a defibrillation pulse primarily depends on the voltage magnitude of the charge stored in the capacitor bank 15 prior to delivery of the defibrillation pulse. The defibrillator 10 modifies the amplitude of defibrillation pulses and, hence, the amount of energy delivered to a patient, by adjusting the voltage level to which the defibrillator's capacitor bank 15 is charged.

In a preferred embodiment of the invention, the memory 21 contains a table of values representing the voltage levels to which the capacitor bank 15 should be charged for different levels of measured TTI. The table is arranged to correlate a voltage level with a measured patient TTI. Accordingly, the defibrillator 10 uses a patient's measured TTI as an index to the table to identify the appropriate voltage level to which its capacitor bank should be charged for delivering a defibrillation pulse to the patient. In actual operation, the microprocessor 23 may use the patient's TTI to generate an appropriate memory address value that is applied to the memory 21. The memory 21 responds by returning the voltage value stored at the memory address. While, if desired, an interpolation algorithm can be used to determine a precise voltage level for each possible measured TTI, it is preferred that ranges of TTI values be used. For example, if a patient TTI measurement lies in a specific range, e.g., 45–50 ohms, a particular voltage value that corresponds with that range is read from the table. If the patient TTI measurement falls in another range, e.g., 70–75 ohms, a different voltage value is read from the table. When using ranges, corrections for quantization errors may be appropriate.

The manner in which voltage values are determined for storing in the table is described later in greater detail. At this point it is sufficient to note that for a given defibrillation pulse shape, the amount of energy that the pulse will deliver to a patient having a particular TTI can be determined. The voltage levels stored in the table are determined by using this relationship in reverse. Knowledge of the amount of energy contained in a pulse produced by a particular capacitor bank voltage level when applied to a patient have a known TTI is used to determine the capacitor bank voltage values stored in memory. This relationship is also applicable in circumstances where, for higher impedance patients, a higher amount of energy is desired. Capacitor bank voltage levels may be determined so that the desired amount of energy is delivered to the patient.

Another aspect of a defibrillation pulse shape is the duration of the pulse. For multiphasic defibrillation pulses, a defibrillator constructed according to the invention determines the duration of one or more of the phases of the pulse. Like controlling the amplitude of a defibrillation pulse controls the energy delivered by the pulse to a patient, controlling the duration of one or more of the phases of a multiphasic defibrillation pulse also controls the amount of energy delivered by the pulse to a patient.

As described more fully below, a patient's TTI is related to phase duration, and thus can be used to set phase duration so that a desired amount of energy is delivered to a patient. Preferably, the memory 21 contains a table of values representing phase durations. The values stored in the table correlate phase duration with measured patient TTI. The defibrillator 10 uses a patient's measured TTI as an index to the table to identify a phase duration appropriate for delivering the desired amount of energy in a defibrillation pulse to the patient. While an interpolation algorithm can be used to determine a precise phase duration for each possible measured TTI, if desired, preferably ranges of TTI values are used. For example, if a patient's TTI lies in a specific range, e.g., 25–50 ohms, a particular phase duration value that corresponds with this TTI range is read from the table. If the patient's TTI falls in another range, e.g., 50–75 ohms, a different phase duration value is read from the table. The manner in which phase duration values are determined for storing in the table is also described in greater detail below.

It is to be understood that a single table may be used for storing voltage level values and phase duration values for different patient TTIs. Such a table allows a single look-up to be used to determine both the capacitor charge voltage value and phase duration value corresponding to a patient's TTI value.

To deliver a defibrillation pulse to a patient, the microprocessor 23 directs defibrillator control circuit 19 to cause the energy source 17, which may be a series of DC batteries, to charge the capacitor bank 15 to the voltage level determined from the look-up table. When the determined voltage level is reached, the microprocessor 23 either instructs the switch 13 to electrically connect the defibrillator capacitor bank to the patient and thereby deliver a defibrillation pulse to the patient, or ignites a light that informs an operator that the defibrillator is ready to deliver a defibrillation pulse to the patient 29. In the latter case, the switch 13 connects the capacitor bank 15 to the patient upon operator activation of a defibrillation control.

The invention described herein is primarily beneficial to defibrillators that generate and deliver defibrillation pulses having truncated exponential waveforms. The preferred truncated exponential waveform is a biphasic truncated exponential (BTE) waveform, the duration of the first phase of which is determined as described herein. Preferably, the duration of the second phase of the BTE waveform is set to equal two-thirds the duration of the first phase.

Phase duration values are derived from a model wherein a patient's physiological response to a defibrillation pulse is simulated as a parallel resistor-capacitor circuit. The amplitude of a defibrillation pulse delivered to a patient decays over a period of time in accordance with a time constant equivalent to the product of the capacitance and the resistance of the defibrillator system (as attached to a patient). The capacitance of a defibrillator system is mostly dictated by the size and configuration of the capacitors in the defibrillator's capacitor bank. The resistance in a defibrillator system is the sum of both the defibrillator's internal resistance and the resistance (i.e., impedance) of the patient. In a paper titled "Choosing the Optimal Monophasic and Biphasic Waveforms for Ventricular Defibrillation", published in the *Journal of Cardiovascular Electrophysiology*, September 1995, the authors Walcott et al. describe a mathematical model that predicts optimal truncation points for monophasic and first phase of biphasic waveforms as the time constant of a defibrillator system varies, to minimize the leading edge voltage needed for successful defibrillation. In this model, an optimal phase duration is calculated to be:

$$\text{duration} = \left[\frac{\tau_s \tau_m}{\tau_s - \tau_m}\right] \ln\left(\frac{\tau_m}{\tau_s}\right) \quad (1)$$

where $\tau_s$ is the time constant of the defibrillator system and $\tau_m$ is a time constant characteristic of a patient's heart. For a preferred embodiment of the invention, $\tau_m$ is selected to equal 0.0051 seconds. Since $\tau_s$ is the time constant of the defibrillator system attached to a patient, $\tau_s$ is mathematically related to patient impedance. As a result, equation (1) relates optimal phase duration to patient impedance.

Phase duration values are calculated for the various levels of patient TTI using equation (1). These phase duration values are stored in the look-up table described earlier. An advantage presented by this invention is that a patient's impedance is measured prior to defibrillation. Performing a predefibrillation measurement allows the phase duration to be determined prior to delivery of the defibrillation pulse.

As noted earlier, the capacitor voltage charge level for a patient TTI value is determined by a reverse calculation of the amount of energy conveyed by a defibrillation pulse to a patient. The purpose of the calculation is to set the capacitor voltage charge to a level that causes a defibrillation pulse produced when the capacitor is discharged to have an energy magnitude that is near or exceeds a chosen energy magnitude. The energy delivered by a truncated exponential waveform to a patient having a 50 ohm TTI may be described as follows:

$$E_{d\varnothing} = \frac{V_\varnothing^2}{2} C \left(\frac{R_\varnothing}{R_\varnothing + R_i}\right)[1 - (1 - t_\varnothing)^2] \quad (2)$$

In this equation, $V_\varnothing$ is the voltage to which the defibrillator capacitor bank is charged for a 50 ohm patient, C is the capacitance of the defibrillator system, $R_\varnothing$ is the resistance of the patient (i.e., 50 ohms), $R_i$ is the internal resistance of the defibrillator, and t is a tilt characteristic of the defibrillation pulse. Tilt is a measure of the pulse amplitude decay and is a ratio of the drop in amplitude to the initial pulse amplitude over a period of time. Tilt may be expressed by the equation:

$$t_\varnothing = 1 - e^{\left[\frac{-d_\varnothing}{(R_\varnothing + R_i)C}\right]} \quad (3)$$

where $R_\varnothing$, $R_i$, and C are as defined earlier and $d_\varnothing$ is the duration of the pulse for a 50 ohm patient. For a BTE waveform having a second phase duration set at two-thirds the duration of the first phase, $d_\varnothing$ equals 1.667 times the duration calculated by equation (1) for the first phase.

For a patient having a TTI different than 50 ohms, a voltage $V_1$ is determined for charging the capacitor bank so that the energy delivered by a defibrillation pulse to the patient ($E_{d_1}$) equals the energy delivered to a 50 ohm patient as described by the above equation for $E_{d_\varnothing}$. Setting $E_{d_1}$ to equal $E_{d_\varnothing}$, substituting $V_1$, $R_1$, and $t_1$ in the equation for $E_{d_1}$, and solving for $V_1$ results in the following equation:

$$V_1 = V_\varnothing \sqrt{\left[\frac{(R_1 + R_i)R_\varnothing}{(R_\varnothing + R_i)R_1}\right]\left[\frac{1 - e^{\left[\frac{-2d_\varnothing}{(R_\varnothing + R_i)C}\right]}}{1 - e^{\left[\frac{-2d_1}{(R_1 + R_i)C}\right]}}\right]} \quad (4)$$

Equation (4) is used to calculate the voltage levels to be stored in the look-up table described earlier for each level of potential patient TTI.

Preferably, a second measure of patient TTI made during delivery of a defibrillation pulse is compared to a first measure of patient TTI made prior to the delivery. It is possible that, due to a change in circumstances, the second measure of patient TTI will vary from the first measure of patient TTI. A variation between measurements may be caused by movement of the defibrillator electrodes 27a and 27b or some component of the defibrillator 10 may have failed. If the second measure is within a certain margin (e.g. 10%) of the first measure, the defibrillator preferably continues forward with the delivery of the defibrillation pulse.

If the second measure of patient TTI varies in excess of the margin but less than a certain threshold (e.g. varies between 10–20%) of the first measure, the second measure of patient TTI may indicate that an error occurred in making the first measure. Since the shape of the defibrillation pulse was determined using the first (erroneous) TTI measure, the amount of energy that will actually be delivered to the patient using the determined pulse shape may not accord with the chosen amount of energy. To compensate for the erroneous TTI measure, the defibrillator may use the second TTI measure to recalculate the duration of the pulse being delivered. Since the initial charge voltage $V_1$ on the capacitor bank had already been set, and the chosen amount of energy $E_{d_1}$ to be delivered is known, the defibrillator may set the variable R1 to equal the second TTI measure and use the mathematical relationship expressed in equations (2) and (3) above to solve for a new pulse duration $d_1$. From this $d_1$, the first phase duration and second phase duration (being two-thirds of the first phase duration) may be adjusted accordingly. By adjusting the phase duration in this manner, it is anticipated that the defibrillation pulse will still deliver the chosen amount of energy to the patient.

If the second measure of patient TTI varies in excess of a threshold (e.g., 20% difference) from the first measure, the second measure may be indicating an open or short connection. In such circumstances, attempting to deliver a defibrillation pulse through the electrodes 27a and 27b may cause significant risk of harm to the patient, the user of the defibrillator, or the defibrillator itself. To avoid possible dangers, the defibrillator 10 preferably discharges the charge stored in the capacitor bank 15 to an energy dump 16 instead the patient 29. Diverting the defibrillation pulse discharge to an energy dump 16 safely dissipates the energy stored in the capacitor bank. Alternatively, the defibrillator 10 may retain the charge in the capacitor bank and not allow a discharge to occur until the electrodes are properly situated on the patient and a patient TTI measurement is made that falls within a certain threshold of the first TTI measure.

The energy dump 16 may be constructed using methods and components known in the art. Resistive elements used in the energy dump 16 should normally be sized to adequately limit the current that would result in the energy dump from receiving a discharge from the capacitor bank 15. Heat dissipating elements may also be required in the energy dump.

In FIG. 2, the energy dump 16 is shown separate from the switch 13. However, in some applications, it is desirable to combine the energy dissipating function of energy dump 16 with a current limiting element (not shown) included in a switch 13. A combined energy dump and current limiting component having both inductive and resistive characteristics used in a switch for generating BTE waveforms is shown and described in copending and commonly assigned U.S. application Ser. No. 09/035,690 titled "H-Bridge Circuit for Generating a High-Energy Biphasic Waveform in an External Defibrillator," incorporated herein by reference.

While the defibrillator 10 is primarily used to provide defibrillation pulses conveying an amount of energy substantially equal to a chosen amount of energy to patients across a range of patient TTI values, the defibrillator 10 may also be used to provide an increased amount of energy in defibrillation pulses delivered to high-impedance patients. It is to be appreciated that controlling the voltage amplitude on the defibrillator capacitor bank in relation to the phase duration of a defibrillation pulse to provide increased magnitude energy pulses has important advantages over prior art systems. Maintaining or increasing defibrillation pulse energy across different patient TTI values makes it more likely that patients with a higher TTI will receive a defibrillation pulse sufficient for defibrillation.

Figure 3:
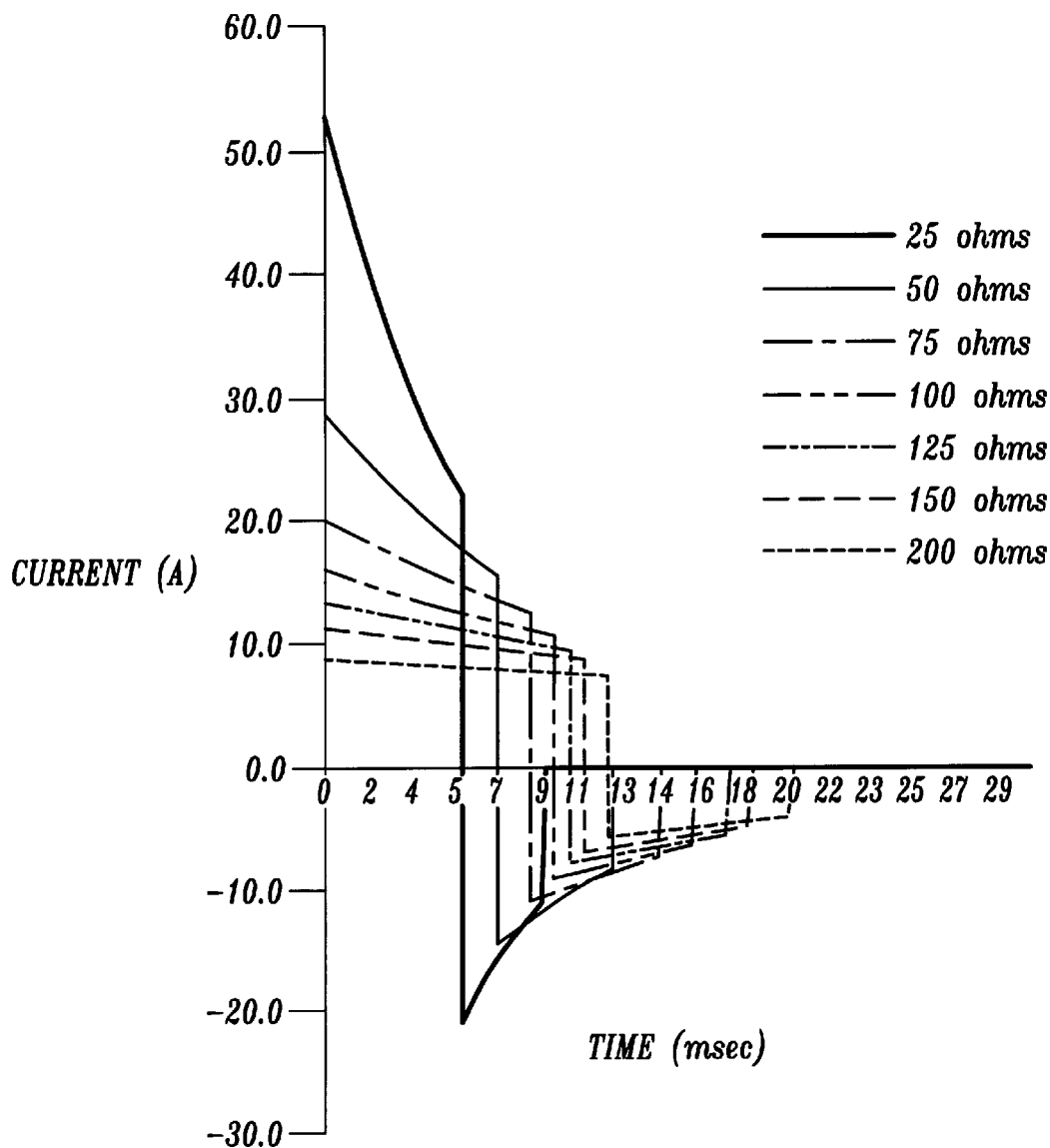
FIG. 3 is a graph depicting the magnitude of the current delivered to each of seven patients by a defibrillator formed in accordance with the present invention, each patient having a different transthoracic impedance, the defibrillator having an energy selection set at 200 joules.
Figure 4:
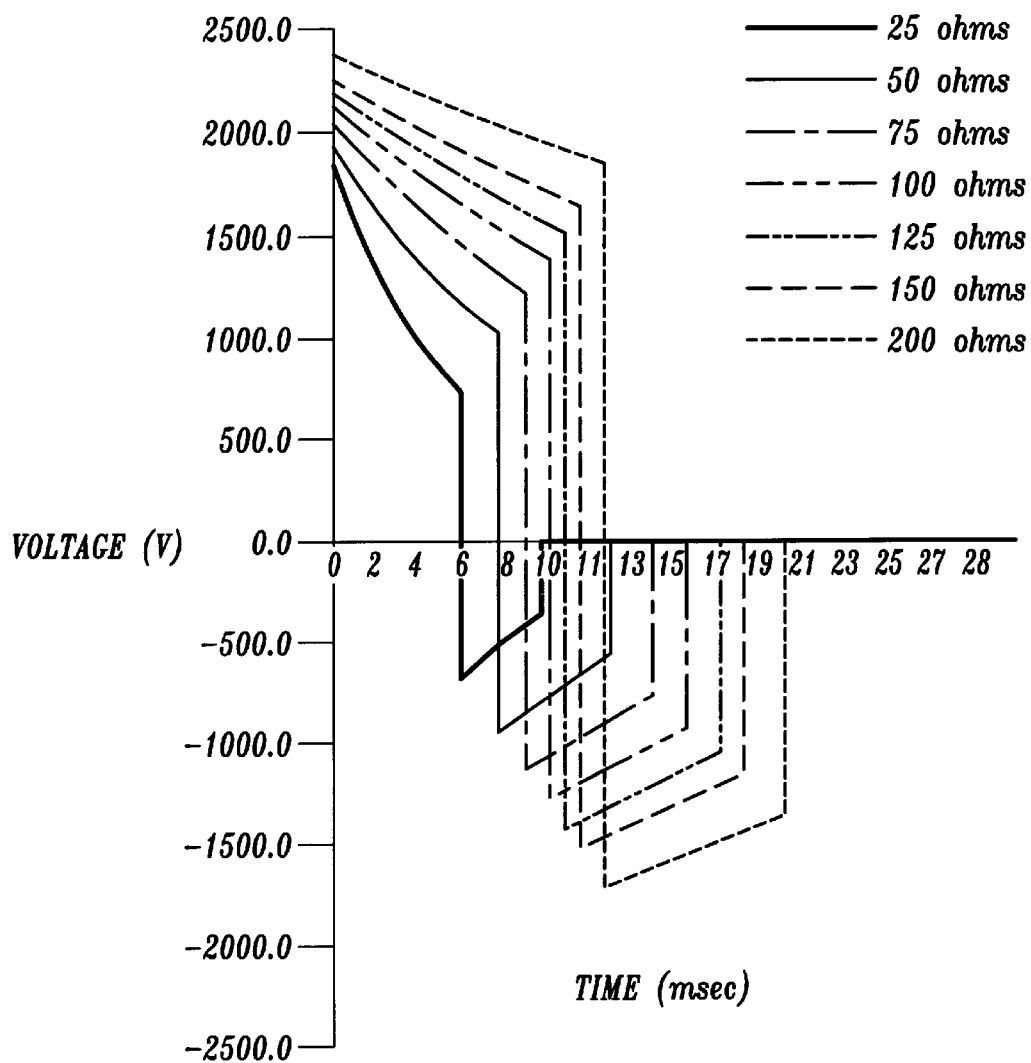
FIG. 4 is a graph showing the magnitude of the voltage delivered across each of seven patients by a defibrillator formed in accordance with this invention, each patient having a different transthoracic impedance, the defibrillator having an energy selection set at 360 joules.

FIGS. 3 and 4 are current and voltage graphs, respectively, that depict how current and voltage levels change in a biphasic truncated exponential (BTE) defibrillator formed in accordance with the invention. The curves shown in FIGS. 3 and 4 represent seven different patients having different TTI values, ranging from 25 ohms to 200 ohms, in 25-ohm increments. FIG. 3 shows how the waveform shape and the amount of current which passes through a patient differs for patients with different TTI values. The curves shown in FIG. 3 were generated by a defibrillator set to supply 200-joule defibrillation pulses. FIG. 4 shows how the waveform shape and the voltage that develops across a patient changes for patients with different TTI values. The curves shown in FIG. 4 were generated by a defibrillator set to supply 360-joule defibrillation pulses. The seven curves shown are for patients having the represented TTI values, again ranging from 25 ohms to 200 ohms, in 25-ohm increments.

Figure 5:
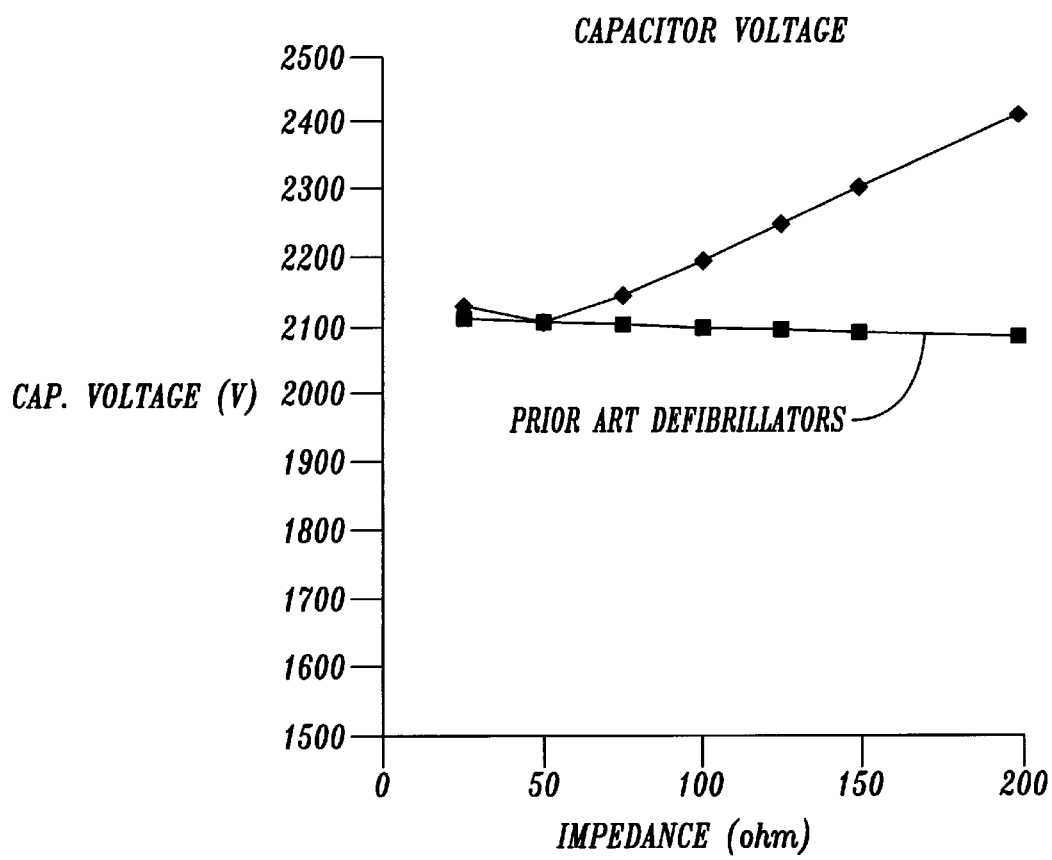
FIG. 5 is a graph depicting the peak voltage to which a defibrillator capacitor bank is charged in a prior art defibrillator and in a defibrillator formed in accordance with the present invention, each having an energy selection set at 360 joules.

As will be appreciated by those familiar with defibrillators, the peak voltage charge to which the capacitor bank is charged will be slightly higher than the peak voltages represented in FIG. 4 due to the voltage drop that occurs across internal impedance of the defibrillator circuitry (see FIG. 5). Accordingly, voltage levels charged on the capacitor bank should range from 1,580 volts to 1,815 volts for a 200-joule pulse to be delivered into 25 ohm to 200 ohm patients, respectively. For a 360-joule pulse, the voltage on the capacitor bank should range between 2,130 volts to 2,440 volts for pulses delivered to patients of 25 ohms to 200 ohms, respectively.

As persons skilled in the art will recognize, the electrical power delivered to a patient is determined by the product of the current flowing through the patient and the voltage developed across the patient. Further, the amount of energy delivered to a patient is determined by integrating the power delivered over the time in which the delivery occurs. Therefore, one skilled in the art can use the curves shown in FIG. 4 to calculate the energy delivered to a patient of each impedance level and establish that the energy delivered to each patient is near or exceeds the nominal energy selected by the operator of the defibrillator, e.g., 200 joules or 360 joules.

Figure 6:
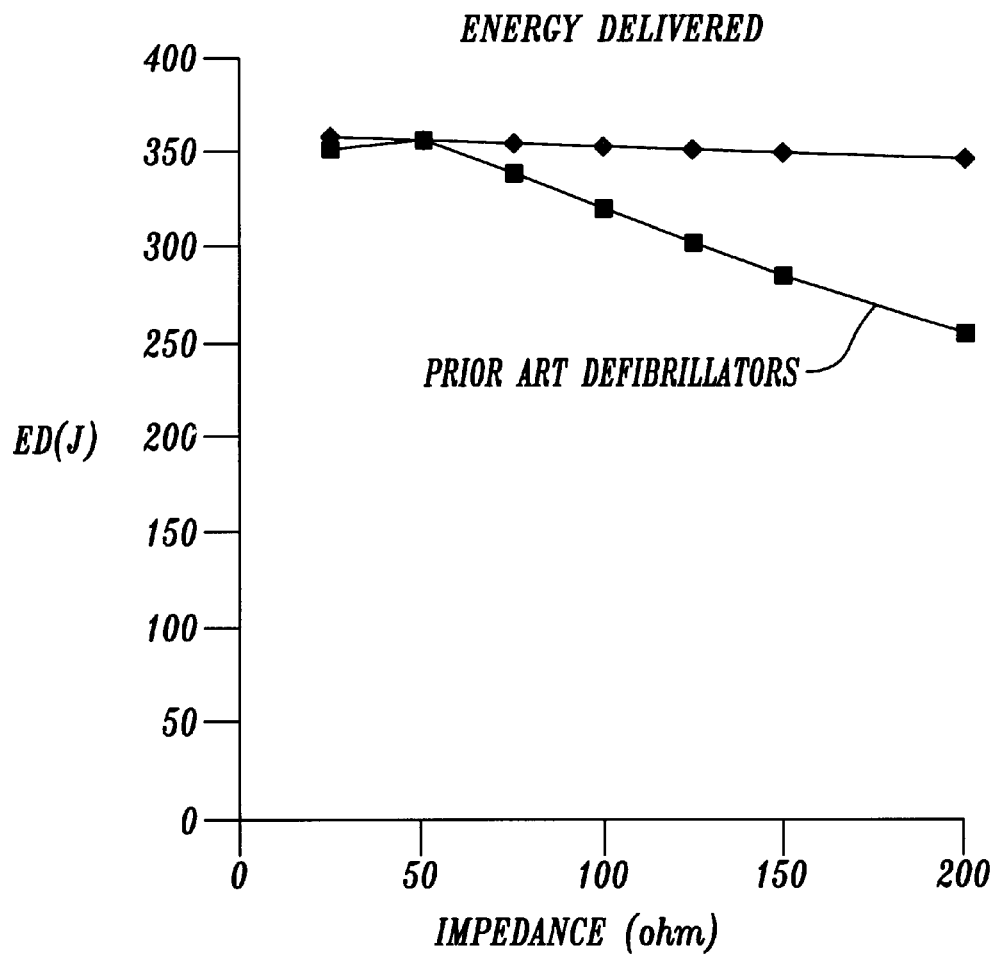
FIG. 6 is a graph showing the energy delivered by a prior art defibrillator and a defibrillator formed in accordance with the present invention, each having an energy selection set at 360 joules.
Figure 7:
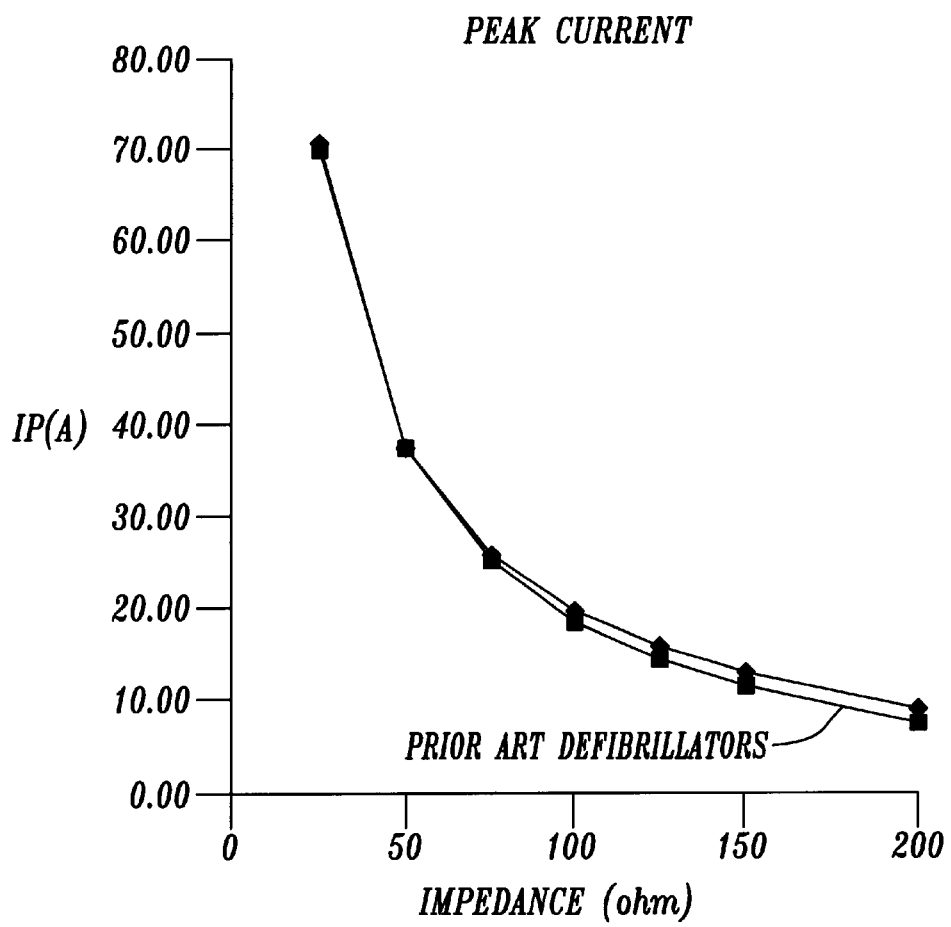
FIG. 7 is a graph showing the peak current delivered by a prior art defibrillator and a defibrillator formed in accordance with the present invention, each having an energy selection set at 360 joules.

FIGS. 5–7 further demonstrate the operation of a defibrillator constructed in accordance with the invention. FIG. 5 shows the voltage to which the defibrillator capacitor bank is charged for a range of patient TTI values. The lower curve shows that the capacitor charge voltage of BTE defibrillators that lack the present invention remains substantially constant regardless of patient impedance. The upper curve shows the increase in capacitor charge voltage in defibrillators employing the present invention. As is evident from the upper curve in FIG. 5, the capacitor charge voltage increases for increasing patient TTI. As noted earlier, rather than being continuous, step voltage changes in voltage based on patient impedance can be employed, if desired.

The result of increasing capacitor charge voltage in accordance with the present invention are demonstrated in FIG. 6. The lower curve of FIG. 6 shows the defibrillation pulse energy delivered by a BTE defibrillator that lacks the present invention. As patient TTI value increases, defibrillator pulse energy delivered to the patient decreases. As shown, patients with a TTI of 200 ohms receive less than 300 joules of energy, even though the energy selector on the defibrillator indicates a desired delivered energy of 360 joules.

The upper curve of FIG. 6 shows the energy delivered to a patient by a defibrillator formed in accordance with the present invention. The upper curve demonstrates that the energy actually delivered to a patient is the same value across all patient TTI values. If the energy level selected is 360 joules, the energy actually delivered is 360 joules.

FIG. 7 shows the peak current that is delivered to patients within the range of TTI values shown in FIGS. 5 and 6. The curves shown in FIG. 7 are for defibrillators having a nominal 360 joules selected energy level. The lower curve shows the peak current delivered to patients using a BTE defibrillator that lacks the present invention. The upper curve shows the amount of current delivered to a patient by a BTE defibrillator constructed in accordance with the invention. As evident from this graph, in the case of patients with higher TTI values, a defibrillator formed in accordance with the present invention delivers a greater peak current. Although providing a specific amount of peak current to patients having a different amount of TTI is not the focus of the present invention, adjusting the voltage level to which the capacitor bank is charged in accordance with the present invention, which produces an adjustment in current delivered, might improve the success rate or efficacy of the defibrillation pulse over a wide range of patient impedance.

While the preferred embodiment of the invention has been illustrated and described, it will be appreciated that various changes can be made therein without departing from the spirit and scope of the invention. It is intended, therefore, that the scope of the invention be determined from the claims that follow and equivalents thereto.

The embodiments of the invention in which an exclusive property or privilege is claimed are defined as follows:

1. A method of delivering a defibrillation pulse to a patient, comprising:
    (a) choosing an amount of energy to deliver to the patient in the defibrillation pulse;
    (b) measuring the patient's transthoracic impedance prior to delivering the defibrillation pulse;
    (c) determining a pulse amplitude and a pulse duration for a phase of the defibrillation pulse prior to delivering the defibrillation pulse to convey an amount of energy to the patient near or exceeding the chosen amount of energy, wherein the pulse duration is determined based on the patient's transthoracic impedance, and the pulse amplitude is determined based on the determined pulse duration, the patient's transthoracic impedance, and the chosen amount of energy;
    (d) charging an energy store to a level in accordance with the determined pulse amplitude; and
    (e) discharging to the patient the charge stored in the energy store to deliver the defibrillation pulse having the determined pulse amplitude and pulse duration.

2. The method of claim 1, further comprising providing an energy selector and wherein choosing the amount of energy to deliver to the patient comprises setting the energy selector to indicate the chosen amount of energy.

3. The method of claim 1, wherein determining a pulse amplitude for the defibrillation pulse includes using the patient's transthoracic impedance measured prior to delivering the defibrillation pulse to determine a voltage level to which the energy store should be charged.

4. The method of claim 3, further comprising providing a memory in which voltage level values are previously stored for use in charging the energy store, the voltage level values being arranged in the memory to correlate with respective patient transthoracic impedances, and referencing the memory using the patient's transthoracic impedance to determine the voltage level value specifying the voltage level to which the energy store should be charged.

5. The method of claim 1, further comprising providing a memory in which duration values are previously stored for use in delivering the defibrillation pulse, the duration values being arranged in the memory to correlate with respective patient transthoracic impedances, and referencing the memory using the patient's transthoracic impedance to determine the duration value specifying the duration for the phase of the defibrillation pulse.

6. The method of claim 1, wherein measuring the patient's transthoracic impedance is performed during delivery of a prior defibrillation pulse delivered to the patient by monitoring an electrical parameter during delivery of the prior defibrillation pulse and calculating the patient's transthoracic impedance based on the monitored electrical parameter.

7. The method of claim 1, wherein the defibrillation pulse is a subsequent defibrillation pulse for delivery after a prior defibrillation pulse and wherein measuring the patient's transthoracic impedance includes:
    (a) monitoring an electrical parameter during delivery of the prior defibrillation pulse to the patient;
    (b) calculating a first measure of the patient's transthoracic impedance based on the monitored electrical parameter;

(c) performing a patient impedance measurement outside of delivering a defibrillation pulse to obtain a second measure of the patient's transthoracic impedance; and (d) calculating the patient's transthoracic impedance based on a combination of the first measure and the second measure.

8. The method of claim 1, wherein measuring the patient's transthoracic impedance prior to delivering the defibrillation pulse results in a first measure, and wherein the method further comprises:

(a) monitoring an electrical parameter during the discharging of the energy store;

(b) calculating a second measure of the patient's transthoracic impedance based on the monitored electrical parameter;

(c) comparing the second measure with the first measure; and (d) if the difference between the second measure and the first measure exceeds a threshold, then discharging the charge stored in the energy store to an energy dump instead of the patient.

9. A defibrillator for delivering a defibrillation pulse to a patient, comprising:

(a) electrodes adapted for placement on the patient;

(b) an impedance measuring circuit for measuring the patient's transthoracic impedance;

(c) a defibrillation pulse generator including an energy store;

(d) a switch in electrical communication with the impedance measuring circuit and the defibrillation pulse generator for selectively connecting the impedance measuring circuit and the defibrillation pulse generator to the electrodes; and (e) a control system in electrical communication with the impedance measuring circuit, the defibrillation pulse generator, and the switch for:

(i) causing the switch to electrically connect the electrodes to the impedance measuring circuit so that prior to delivery of the defibrillation pulse, the impedance measuring circuit measures the transthoracic impedance of a patient coupled to the electrodes;

(ii) determining a pulse amplitude and a pulse duration for a phase of the defibrillation pulse to be delivered to the patient to convey an amount of energy to the patient near or exceeding a previously chosen amount of energy, wherein the pulse duration is determined based on the patient's transthoracic impedance, and the pulse amplitude is determined based on the determined pulse duration, the patient's transthoracic impedance, and the chosen amount of energy;

(iii) causing the defibrillation pulse generator to charge the energy store to a level in accordance with the determined pulse amplitude; and (iv) causing the switch to electrically connect the electrodes to the defibrillation pulse generator so that the charge stored on the energy store discharges to deliver the defibrillation pulse to the patient.

10. The defibrillator of claim 9, wherein the level to which the energy store is charged is selected from a set of voltage levels, and the control system uses the patient's transthoracic impedance to determine which voltage level of the set of voltage levels to use in charging the energy store.

11. The defibrillator of claim 10, wherein each voltage level of the set of voltage levels corresponds to a range of transthoracic impedance values, and the selected voltage level corresponds to the range of transthoracic impedance values that includes the patient's transthoracic impedance.

12. The defibrillator of claim 10, wherein the defibrillator further includes a memory in communication with the control system, the set of voltage levels being stored in the memory, and wherein the control system uses the patient's transthoracic impedance in referencing the memory to select a voltage level for use in charging the energy store.

13. The defibrillator of claim 9, wherein the defibrillator further includes an energy selector in communication with the control system for permitting selection of an energy level as the chosen amount of energy.

14. The defibrillator of claim 9, wherein the discharge of the charge stored in the energy store is controlled so that delivery of the defibrillation pulse occurs for a duration selected from a set of durations based on the patient's transthoracic impedance measured prior to delivering the defibrillation pulse.

15. The defibrillator of claim 14, wherein the defibrillator further includes a memory in communication with the control system, the set of durations being stored in the memory, and wherein the control system uses the patient's transthoracic impedance in referencing the memory to select a duration for use in delivering the defibrillation pulse.

16. The defibrillator of claim 9, further comprising an energy dump in electrical communication with the energy store for receiving and dissipating electrical energy, wherein the control system causes the charge stored in the energy store to be discharged into the energy dump instead of the patient if a measurement of the patient's transthoracic impedance made during delivery of the defibrillation pulse varies in excess of a threshold from the impedance measurement made by the impedance measuring circuit prior to delivery of the defibrillation pulse.

17. A method of determining a pulse shape for a defibrillation pulse to be delivered from an energy store to a patient, comprising:

(a) measuring the patient's transthoracic impedance prior to delivering the defibrillation pulse;

(b) determining a duration for a phase of the defibrillation pulse based on the patient's transthoracic impedance; and (c) determining a voltage level to which the energy store is charged for determining a pulse amplitude of the defibrillation pulse, wherein the voltage level is based on the patient's transthoracic impedance, the determined duration, and a previously chosen amount of energy, wherein the defibrillation pulse having the determined pulse duration and amplitude conveys an amount of energy to the patient that is near or exceeds the chosen amount of energy.

18. The method of claim 17, wherein determining a voltage level to which the energy store is charged includes using the patient's transthoracic impedance in referencing a memory in which values representing voltage levels are stored, and selecting from the memory a voltage level value corresponding to the patient's transthoracic impedance for specifying the voltage level to which the energy store is charged.

19. The method of claim 17, wherein determining a duration for a phase of the defibrillation pulse includes using the patient's transthoracic impedance in referencing a memory in which duration time values are stored, and selecting from the memory a duration time value corresponding to the patient's transthoracic impedance for specifying the duration for a phase of the defibrillation pulse.

20. The method of claim 17, wherein measuring the patient's transthoracic impedance prior to delivering the defibrillation pulse includes combining an impedance measurement made during a prior defibrillation pulse delivered to the patient with an impedance measurement made outside of delivery of the prior defibrillation pulse.

* * * * *